(12) United States Patent
Furrer et al.

(10) Patent No.: US 10,149,929 B2
(45) Date of Patent: Dec. 11, 2018

(54) BREAST SHIELD UNIT WITH MEDIA SEPARATION

(71) Applicant: MEDELA HOLDING AG, Baar (CH)

(72) Inventors: Etienne Furrer, Zug (CH); Mario Rigert, Buchrain (CH); André Schlienger, Maschwanden (CH)

(73) Assignee: MEDELA HOLDING AG, Baar (CH)

( * ) Notice: Subject to any disclaimer, the term of this patent is extended or adjusted under 35 U.S.C. 154(b) by 161 days.

(21) Appl. No.: 14/651,506

(22) PCT Filed: Dec. 12, 2013

(86) PCT No.: PCT/CH2013/000220
§ 371 (c)(1),
(2) Date: Jun. 11, 2015

(87) PCT Pub. No.: WO2014/094187
PCT Pub. Date: Jun. 26, 2014

(65) Prior Publication Data
US 2015/0328380 A1  Nov. 19, 2015

(30) Foreign Application Priority Data
Dec. 18, 2012  (CH) ...................................... 2839/12

(51) Int. Cl.
*A61M 1/00* (2006.01)
*A61M 1/06* (2006.01)

(52) U.S. Cl.
CPC ............ *A61M 1/0049* (2013.01); *A61M 1/06* (2013.01); *A61M 1/064* (2014.02); *A61M 1/066* (2014.02)

(58) Field of Classification Search
CPC .. A61M 1/0049; A61M 1/0066; A61M 1/064; A61M 1/0064; A61M 1/06; A61M 2205/75
See application file for complete search history.

(56) References Cited

U.S. PATENT DOCUMENTS

| 2004/0087898 A1* | 5/2004 | Weniger ................ A61M 1/066 604/74 |
| 2007/0060873 A1* | 3/2007 | Hiraoka .............. A61M 1/0066 604/74 |

(Continued)

FOREIGN PATENT DOCUMENTS

| EP | 1034807 A1 | 9/2000 |
| EP | 2308523 A1 | 4/2011 |

(Continued)

OTHER PUBLICATIONS

International Search Report for Application No. PCT/CH2013/000220, dated Mar. 13, 2014.

(Continued)

*Primary Examiner* — Edelmira Bosques
*Assistant Examiner* — Hamza A Darb
(74) *Attorney, Agent, or Firm* — Marshall, Gerstein & Borun LLP

(57) ABSTRACT

A breastshield unit for use with a breastpump for expressing human breastmilk has a breastshield for receiving a mother's breast and a media separation device for transferring a vacuum into the interior of the breastshield. The breastshield has a receiving area for receiving a nipple of the mother's breast. The media separation device has a media separation membrane which, for the purpose of transferring the vacuum, is movable to and fro between two positions. The media separation membrane is located in the receiving area at least in one of the two positions. Despite the integrated media separation, the breastshield unit can be made extremely compact and minimizes the dead volume.

15 Claims, 5 Drawing Sheets

(56) References Cited

U.S. PATENT DOCUMENTS

2010/0121267 A1* 5/2010 Silver ............... A61M 1/06
 604/74
2011/0071466 A1* 3/2011 Silver ............... A61M 1/06
 604/74

FOREIGN PATENT DOCUMENTS

| EP | 2441481 A1 | 4/2012 |
|---|---|---|
| WO | WO-2008/057218 A2 | 5/2008 |
| WO | WO-2011/037841 A2 | 3/2011 |

OTHER PUBLICATIONS

International Preliminary Report on Patentability for Application No. PCT/CH2013/00020, dated Jul. 2, 2015.

* cited by examiner

BREAST SHIELD UNIT WITH MEDIA SEPARATION

CROSS-REFERENCE TO RELATED APPLICATION

The present application is the US national phase of International Patent Application No. PCT/CH2013/000220, filed Dec. 12, 2013, which application claims priority to Switzerland Application No. CH 2839/12, filed Dec. 18, 2012. The priority application, CH 2839/12, is hereby incorporated by reference.

TECHNICAL FIELD

The present invention relates to a breastshield unit for use with a breastpump for expressing human breastmilk and to a media separation device.

PRIOR ART

Breastpumps for expressing human breastmilk by means of underpressure are well known. Manually operated breastpumps and motor-driven breastpumps are commercially available. They are connected to a breastshield either directly or via a vacuum line. The breastshield is placed onto the mother's breast from which milk is to be expressed, in such a way that at least the nipple, and in most cases also the areola and the surrounding tissue of the mother's breast, are sealingly enclosed. The breastshield is usually connected to a milk collection container, either directly or via a milk line, such that expressed milk can flow directly into this container.

Moreover, media separation devices for breastpumps are known. They serve to protect the vacuum pump from being contaminated by milk.

US 2004/0087898 discloses a breastshield unit with a coupling part for connection to a breastpump. A flexible media separation membrane is arranged in this attachment part and transfers the applied vacuum into the hollow interior of the breastshield funnel and at the same time separates a milk flow path in the breastshield from a vacuum connector opening.

WO 2008/057218 and WO 2011/037841 likewise disclose media separation membranes of this kind that are arranged in a coupling part.

Although these media separation devices afford advantages as regards protecting the suction line and the breastpump, they hugely increase the volume of the breastshield. This is unsuitable particularly in what are referred to as "hands-free" solutions, in which the breastshield is worn in a bra under the clothes.

DISCLOSURE OF THE INVENTION

It is therefore an object of the invention to make available a breastshield unit, with a media separation device, which is as compact and small as possible.

The breastshield unit according to the invention, for use with a breastpump for expressing human breastmilk, has a breastshield for receiving a mother's breast and a media separation device for transferring a vacuum into the interior of the breastshield. The breastshield unit has a receiving area for receiving a nipple of the mother's breast. The media separation device has a media separation membrane which, for the purpose of transferring the vacuum, is movable to and fro between two positions. According to the invention, the media separation membrane is located in the receiving area at least in one of the two positions or, when it is arranged under the receiving area, it adjoins it.

Since the media separation membrane is arranged in the area of the nipple, the breastshield unit can be made extremely compact and small despite the media separation device. Another important advantage is that the dead volume, i.e. the volume to be evacuated in the breastshield during the expression of milk, is further minimized.

The area for receiving the nipple, and the area of movement of the media separation membrane needed to transfer the vacuum, partly share the same physical space. However, the nipple and the membrane do not interfere with each other, since the movements take place synchronously. In other words, when the membrane moves away from the breast, the nipple moves towards the membrane, on account of the vacuum transferred to the receiving area, and also has enough space to expand, since the membrane has moved sufficiently far from the receiving area. When the membrane then expands back into the receiving area on account of the cyclical pumping movement of the vacuum pump, the nipple returns approximately to its natural length on account of the increase of pressure in the receiving area. Therefore, the membrane is not impeded in its movement, and it can expand to the maximum extent into the receiving area. There is therefore no danger of the function of the media separation membrane being impaired. Moreover, the risk of the media separation membrane touching the nipple or adhering to it, and thus suppressing the flow of milk, is practically nonexistent.

In a preferred embodiment, the media separation membrane is arranged on the rear face of the breastshield device, the rear face being located at an artificial continuation of the mother's breast. Breastshield units of this kind can be produced easily and inexpensively.

In a preferred embodiment, a tubular stub is present which forms the receiving area and which has an end, wherein the media separation membrane is arranged directly on this end. The stub is preferably a part of the breastshield or of a breastshield insert.

In a preferred embodiment, the breastshield unit has an attachment for connection to a milk collection container, wherein the media separation membrane is arranged approximately perpendicularly with respect to this attachment. Here, "approximately perpendicularly" is also understood as an angle differing by 0° to 20°, preferably by 0° to 5°, from a right angle.

In another preferred embodiment, a milk flow path is present which leads from the receiving area of the breastshield to an attachment for connection to a milk collection container, wherein the media separation device is arranged in this milk flow path. The media separation membrane preferably interrupts and re-opens the milk flow path according to a cyclically applied underpressure. This reduces the dead volume.

In a preferred embodiment, the receiving area, in particular of the breastshield or of the breastshield insert, has a wall which is provided with apertures, wherein the media separation membrane is arranged on an outer face of this wall in the area of the apertures. In this way, the risk of the media separation membrane adhering to the nipple is definitively avoided.

In a preferred embodiment, the breastshield unit has an attachment for connection to a milk collection container, wherein the media separation membrane is arranged approximately horizontally with respect to this attachment.

Here, "approximately horizontally" is also understood as an angle of inclination of 0° to 20°, preferably 0° to 5°.

The three above variants have the advantage that the breastshield unit can be made extremely short and compact in the longitudinal direction of the breastshield. The media separation device is located under the receiving area for the nipple and therefore does not lengthen the breastshield. This variant is advantageous in particular in "hands-free" units that are worn under a bra. These variants are also extremely inexpensive to produce and, therefore, can also be sold as disposable products.

In a preferred embodiment, a check valve is present which separates the receiving area from an attachment for connection to a milk collection container, wherein the check valve is formed in one piece with the media separation membrane. This reduces the production costs.

In a preferred embodiment, the media separation device as a whole is arranged to be movable in the longitudinal direction relative to the breastshield. This is an independent invention, in which the media separation membrane can also be arranged spaced apart from the receiving area for the nipple.

Preferably, the breastshield unit also has a breastshield insert which can be secured in the breastshield, wherein the media separation device is suspended movably by means of this breastshield insert in the breastshield.

In a preferred embodiment, the breastshield has guide slits which extend in a longitudinal direction of the breastshield and along which the media separation device as a whole is movable. The movement is guided and limited in this way.

Preferably, the media separation device has a dimensionally stable housing, wherein the media separation membrane is held movably therein.

In a preferred embodiment, the breastshield has a rear opening at an end directed away from the mother's breast, as a result of which the media separation device is manually movable, in particular pushable, in the longitudinal direction towards the mother's breast by access through this rear opening. This makes it easier to apply and adapt the breastshield unit to the mother's breast, particularly when a breastshield or a breastshield insert with a flexible breast pad is used. Preferably, the media separation device is suspended on the housing by means of the flexible breast pad. In a preferred embodiment, this suspension is achieved by means of a peripheral securing collar of the breast pad being turned back over a flange of the breastshield. The breast pad can be pressed forwards out of the breastshield. It can even be turned inside out depending on its shape. If the breast pad is now applied to the breast, it automatically assumes the shape of the breast. Depending on the shape of the breast pad, the breast pad can turn back into this shape adapted to the breast.

In a preferred embodiment, the breastshield is dimensionally stable. The breastshield unit also has a flexible breastshield insert for insertion into the breastshield, wherein the breastshield has a first, open breastshield end for placing onto a mother's breast, and wherein the breastshield insert has a first and a second insert end which define a longitudinal direction. The first, open breastshield end has a peripheral edge on which the breastshield insert can be secured or is secured with the first insert end, wherein the breastshield insert, in the assembled state, extends from this first insert end in the interior of the breastshield to the second insert end. The breastshield insert, between the first and second insert ends, extends substantially spaced apart from the breastshield, wherein the second insert end, in the assembled state of the breastshield insert, is movable in the longitudinal direction relative to the breastshield. The media separation device is preferably connected to the second insert end.

This embodiment prevents the mother from applying excessive pressure and/or unevenly distributed pressure to the breastshield and, therefore, to the breast. This would eventually cause pain and prevent an optimal flow of milk from the breast.

In one embodiment, the media separation device according to the invention has a dimensionally stable housing and a media separation membrane arranged therein. The housing has a tubular receiver for receiving a breastshield or a flexible breastshield insert insertable into a breastshield, wherein this receiver defines a receiving area for receiving a nipple of a mother's breast, and wherein the media separation membrane adjoins this receiver or protrudes into it.

BRIEF DESCRIPTION OF THE DRAWINGS

Preferred embodiments of the invention are described below with reference to the drawings, which are provided only for explanatory purposes and are not to be interpreted as limiting the invention. In the drawings.

Identical parts are designated by identical reference signs in the figures.

DESCRIPTION OF PREFERRED EMBODIMENTS

Figure 1:
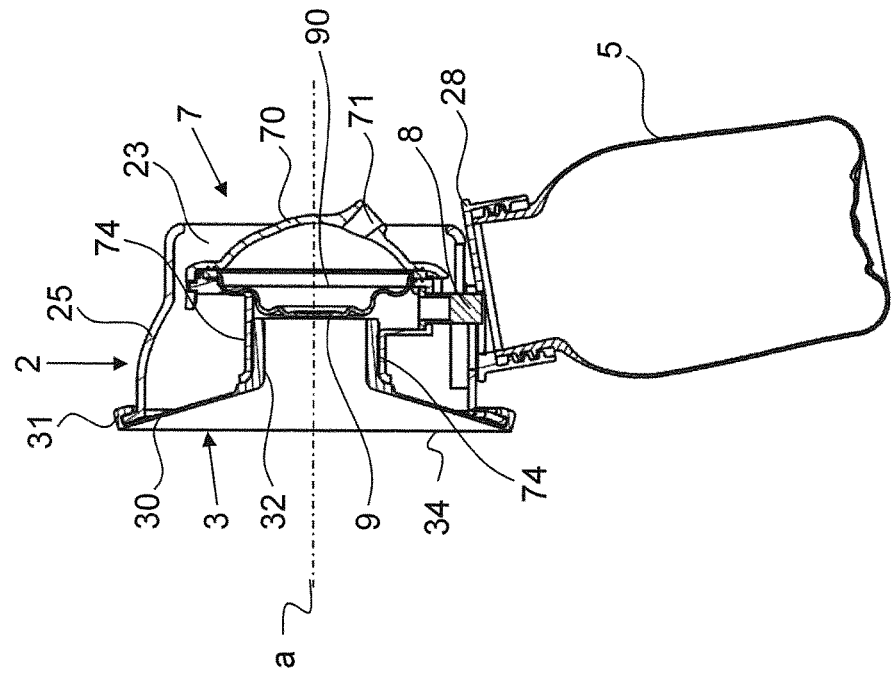
FIG. 1 shows a longitudinal section through a breastshield unit according to the invention, mounted on a milk collection container, in a first embodiment.

FIG. 1 shows a first illustrative embodiment of a breastshield unit according to the invention. It has a breastshield 2 and a media separation device 7 connected thereto.

In this embodiment, the breastshield 2 has a dimensionally stable or stiff main body 25, preferably made of plastic. A housing 70 of the media separation device 7 is held in this main body 25. As is shown in the illustrative embodiment below, the housing 70 can be arranged movably in the main body 25. However, it can also be connected rigidly and immovably thereto.

The main body 25 has a milk attachment part 28 with a milk outlet opening, which serves for connection to a milk collection container 5. A valve 8, preferably a check valve, is arranged on the housing 70 of the media separation device or also on the milk attachment part 28, in order to limit the dead volume when expressing milk and to prevent the expressed milk from flowing back. In this example, a duckbill valve is shown.

The milk attachment part 28 and the milk collection container 5 can also have another shape. The milk attachment part 28 can also be a component of the media separation device 7, or it can be designed as a lid of the milk collection container. Bottles or bags, for example, can be used as milk collection container.

A breastshield insert 3 is arranged in the breastshield 2. It is preferably made of a flexible material, in particular of silicone. It has a breast pad 30, here in the shape of a funnel which, at the end near the breast, bears on the main body 25 or is secured releasably on the latter. The breast pad 30 merges preferably in one piece into a stub 32, which is secured on the housing 70 of the media separation device 7 in this example. This type of securing is particularly advantageous when, as is explained below, the media separation device 7 is movable relative to the main body 25 of the breastshield 2. The securing can be done in different ways. In this example, the stub 32 has a flange 320 which is directed away from the breast and which is held, in particular snap-fitted, in a corresponding receiver of the housing 70.

The breast pad 30 is preferably at least partially elastic. However, it can also be dimensionally stable or even stiff. The stub 32 is preferably more dimensionally stable, for example by virtue of the fact that, although it is made of the same material as the breast pad 30, it has a greater wall thickness.

The breast pad 30 serves the purpose of being placed onto a mother's breast, with the nipple of the breast extending right into the stub 32. In this way, the stub 32 forms, with its hollow interior, a receiving area 33 for receiving the nipple.

The housing 70 of the media separation device 7 is preferably stiff or dimensionally stable and is in particular made of plastic. A vacuum connector 71 for connection to a vacuum pump (not shown) is present on the housing 70 of the media separation device 7. The connection can be made directly or via a suction line. The vacuum pump can be driven manually or by motor. On the housing 70, there is also a milk outlet opening 77, which is closed by said valve 8. In embodiments described further below, this milk outlet opening is arranged in a breastshield insert receiver 74 of the media separation device. A milk flow path is thus formed through which expressed breast milk can pass from the receiving area 33 through the milk outlet opening 77, the valve 8 and the milk outlet 28 of the main body 25 into the milk collection container 5.

The media separation device 7 has a media separation membrane 9, which is held movably in the housing 70. In this example, it is clamped between the housing 70 and a flange 320 at the end of the stub 32 directed away from the breast. The media separation membrane 9 forms a breast-side wall of a pump chamber 90, and the housing 70 forms the wall of the pump chamber 90 directed away from the breast. The media separation membrane 9 is preferably made of silicone.

It serves to ensure that a cyclically changing underpressure applied via the vacuum connector 71 is transferred into the receiving area 33 of the breastshield insert 3 or of the breastshield 2. When an underpressure is conveyed cyclically into the pump chamber 90 via the vacuum connector 71, the media separation membrane 9 moves synchronously with this and transfers the underpressure into a hollow space formed by the breastshield insert 3 and the mother's breast B. Milk is expressed. The media separation membrane 9 prevents expressed milk from passing into the pump chamber 90 and from there to the vacuum source. Instead, the milk flows through the milk outlet opening 77, arranged before the membrane 9, into the milk collection container 5.

The media separation membrane 9 thus moves to and fro between two positions. The first position is not shown in the figures. It is directed away from the breast and is reached when an underpressure is applied. In this first position, the media separation membrane 9 is located in the rear area of the pump chamber 90, i.e. at the rear wall of the housing 70. The second position is shown in the figures. It is directed towards the breast.

The media separation membrane 9 is arranged such that it is located in the receiving area 33 in at least one of these two positions. It usually protrudes into this receiving area 33 at least in the second position directed towards the breast and it thus minimizes the dead volume in said hollow space.

FIGS. 2 to 8 show another illustrative embodiment. Identical parts are provided with the same reference signs as in the first example.

In this embodiment, the breastshield 2 likewise has a housing-shaped main body 25. The breastshield 2 likewise serves for bearing on the mother's breast B and at the same time for connecting to the milk collection container 5. It likewise has a milk attachment part 28 with which it can be connected to the milk collection container 5. The breastshield 2 is preferably stiff or dimensionally stable and in particular is made of plastic. The same applies to the housing 70 of the media separation device, which is arranged in the main body 25.

The milk outlet opening 77, provided with the check valve 8, leads via a through-opening 29 of the main body 25 into the milk collection container 5.

A breastshield insert receiver 74 is formed integrally on the housing 70 of the media separation device 7 and forms a receiving stub for the stub 32 of the insert 3. In this embodiment, the stub 32 is designed as a free end and has no flange directed away from the breast. The stub 32 of the insert 3 is held non-displaceably in this receiver 74 during use. It is held with an interference fit, for example, and can be removed for cleaning or replacement. However, the stub 32 can also be connected to the media separation device 7 such that it cannot be released without destruction. A securing collar 31 formed integrally on a first insert end 34 of the insert 3 is turned back over a flange 22 of the main body 25 of the breastshield 2.

The insert 3 preferably has a design similar to the insert according to the first example. Preferably, the pad area 30 has a slightly funnel-shaped configuration. It can also be configured more or less, or entirely, as a flat plane. The length of the pad area 30 is preferably relatively short, i.e. many times shorter than the overall length of the insert 3.

Figure 5:
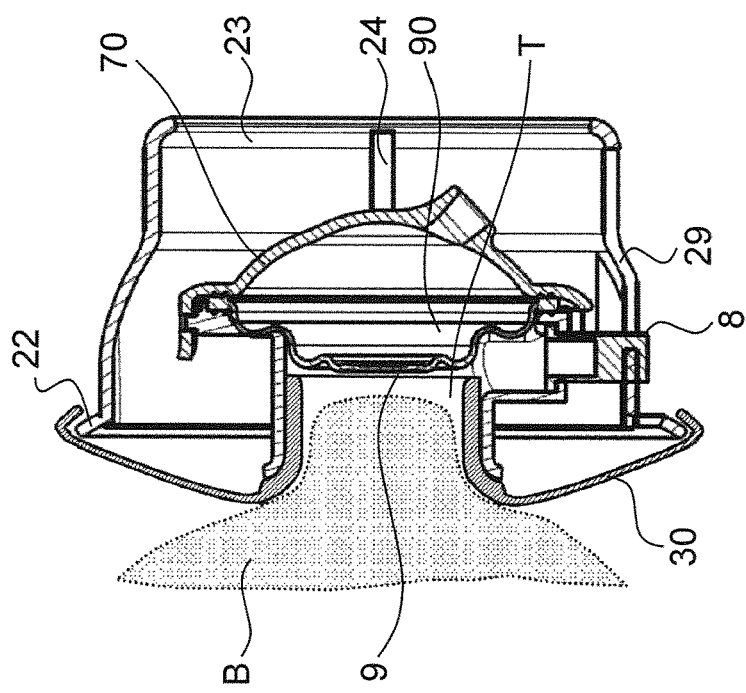
FIG. 5 shows the breastshield unit according to FIG. 3 when being placed on a mother's breast.

As can be seen in FIG. 5, the media separation membrane 9, even in the undeflected state, reaches approximately or exactly as far as the end of the stub 32 of the insert 3. It will be seen in FIG. 7 that the stub 32 is dimensioned in such a way that, with a breast and nipple of a size in the normal range, it is filled along its entire length by the nipple. However, during the expression of milk, the media separation membrane 9 preferably does not touch the nipple, and instead they move synchronously in the same direction.

The media separation device 7 is preferably arranged movably, in particular displaceably in the main body 25 of the breastshield 2. This can also be the case in the example according to FIG. 2.

For this purpose, the main body 25 has guide slits 24, in which guide lugs 76 of the housing 70 engage. This can be seen in FIG. 4, for example. The media separation device 7 is displaceable along these slits 24. The slits 24 can be rectilinear or curved. They are rectilinear in this example. The valve 8 and the milk outlet opening 77 lead into the milk collection container 5 in all positions of the media separation device 7 relative to the main body 25, since the through-opening 29 is larger than the valve 8 and the milk outlet opening 77. The through-opening 29 is preferably designed as an oblong hole.

The rear end of the main body 25, directed away from the breast, is open. The media separation device 7 is manually movable via this rear opening 23, specifically displaceable in this case along the slits 24.

Figure 2:
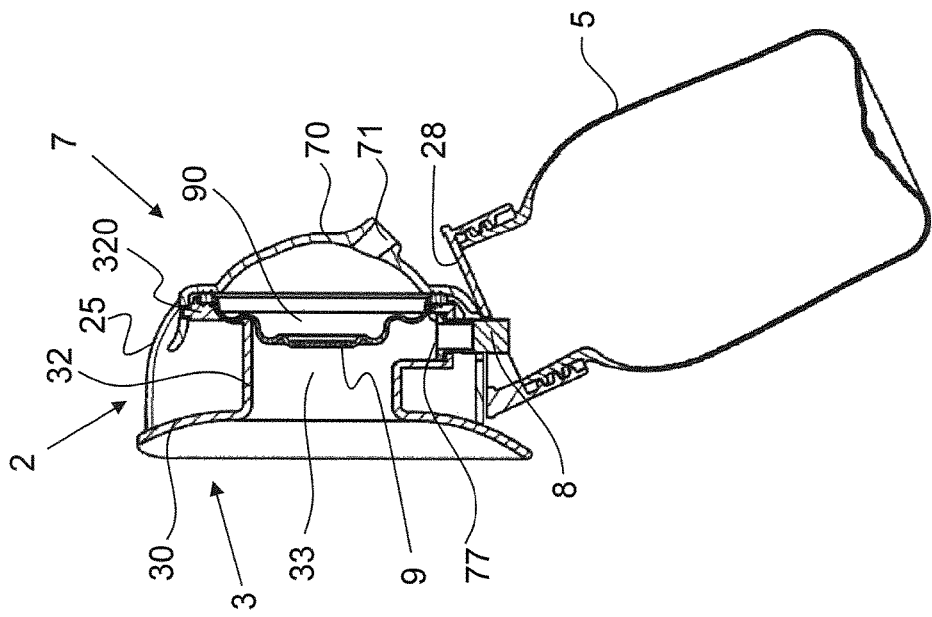
FIG. 2 shows a longitudinal section through a breastshield unit according to the invention, mounted on a milk collection container, in a second embodiment.
Figure 4:
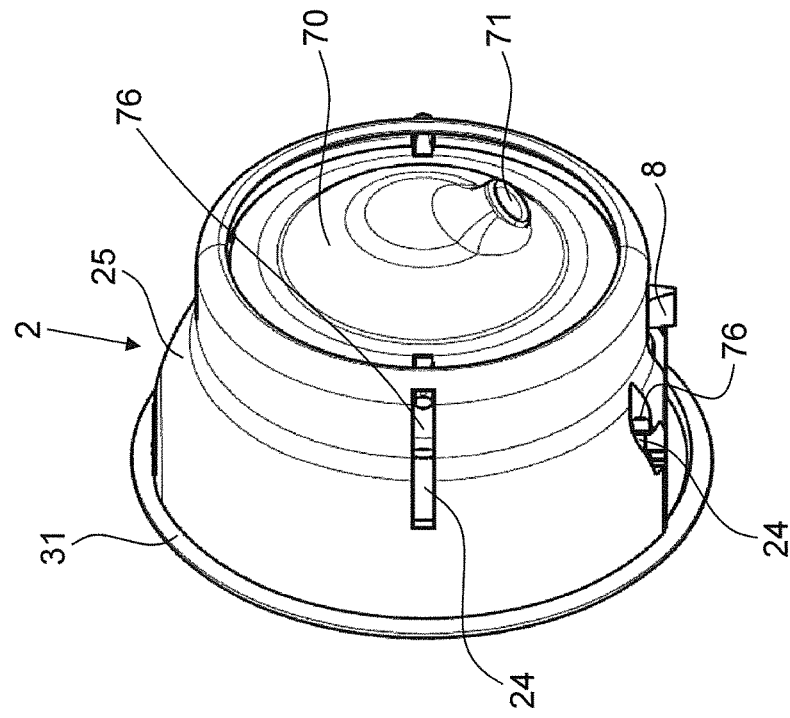
FIG. 4 shows a perspective view of the breastshield unit according to FIG. 2 in a first position.
Figure 3:
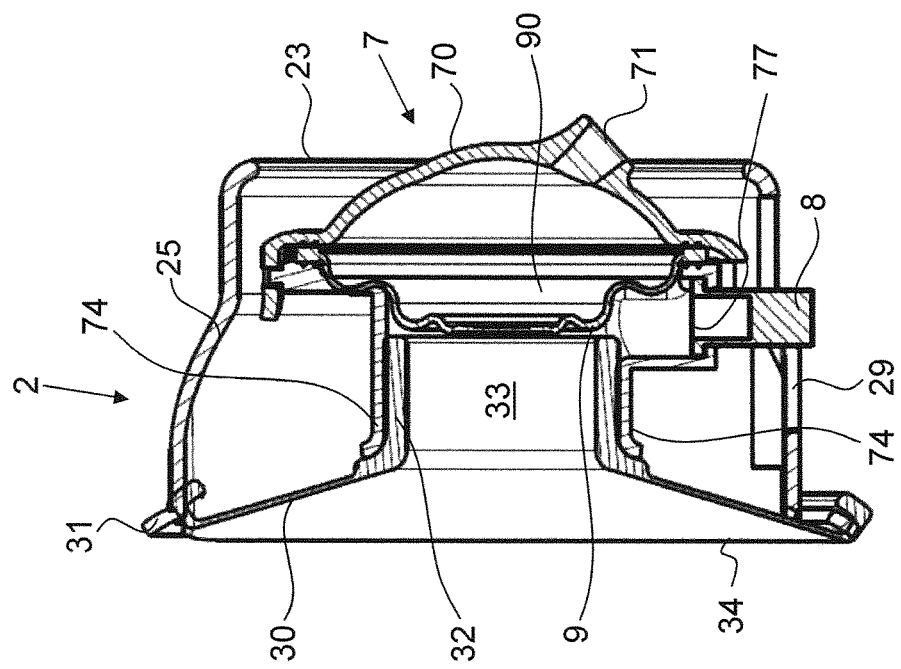
FIG. 3 shows the breastshield unit according to FIG. 2 in an enlarged view.

In FIGS. 2 to 4, the breastshield unit is shown in the state when not yet used or when not currently in use. The media separation device 7 protrudes through the rear opening 23 or is located at least in a rear area. The breast pad 30 of the insert 3 is relaxed or undeflected and is slightly funnel-shaped in this example.

Figure 6:
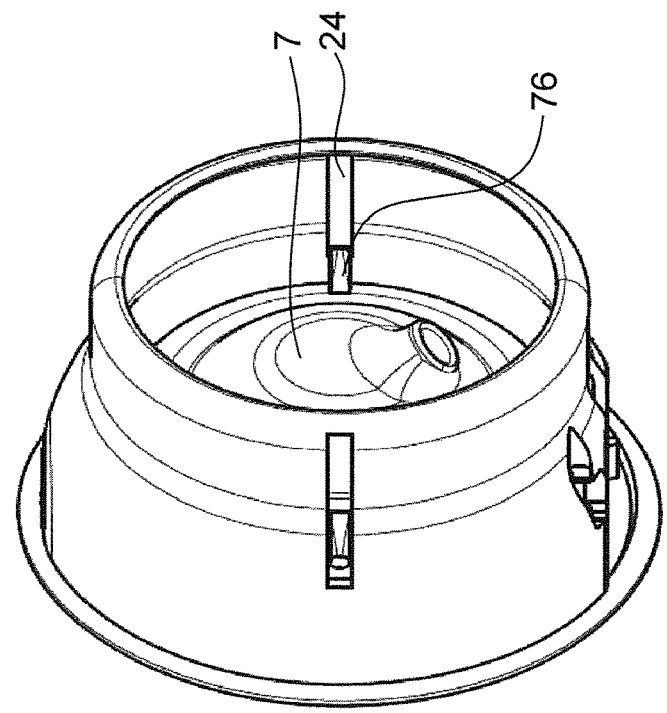
FIG. 6 shows a perspective view of the breastshield unit in the position according to FIG. 5.
Figure 7:
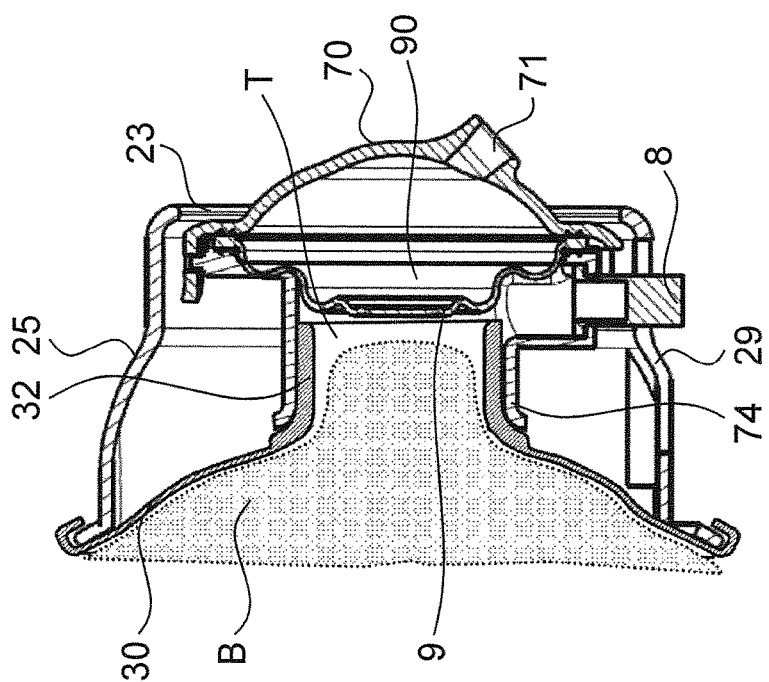
FIG. 7 shows the breastshield unit according to FIG. 3 when placed on the mother's breast.

In order to use the breastshield unit, the media separation device 7 is pushed forwards by hand, as is shown in FIGS. 5 and 6. The breast pad 30 of the insert 3 is extended, being pushed out to the front, according to requirements, towards the mother's breast B. The nipple can be received optimally in the receiving opening 33. If the manual pressure on the housing 70 is now stopped, but the main body 25 is held as before on the breast by hand, in a bra or another holding device, the housing 70 slides back along the slits 24 and the insert 3 lies sealingly, but without excessive pressure, on the breast B. This is shown in FIG. 7. Expressing milk can now begin.

The second insert end of the breastshield insert 3, i.e. the stub 32, is therefore movable relative to the breastshield 2, this movement taking place together with the media separation device 7.

Figure 8:
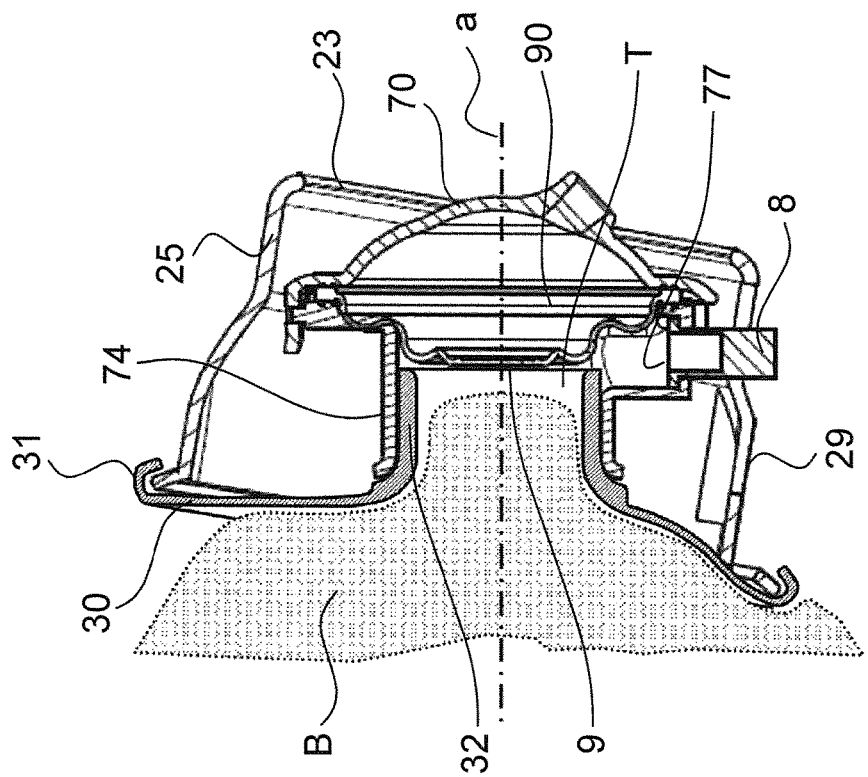
FIG. 8 shows the breastshield unit according to FIG. 3 in an inclined position.

Depending on the shape of the guide slits 24, it is also possible to incline the media separation device 7 relative to the breastshield 2. This is shown in FIG. 8. It can preferably be inclined in different directions.

In the two abovementioned embodiments, the media separation membrane 9 is arranged approximately perpendicularly with respect to the attachment part 28, i.e. approximately perpendicularly with respect to the longitudinal direction a of the breastshield 2 and of the breastshield insert 3.

By contrast, in the two illustrative embodiments described below, the media separation membrane is arranged approximately horizontally, i.e. approximately parallel to the milk attachment part or in the milk flow path.

FIG. 9 once again shows a breastshield 2 according to the invention with a media separation membrane 9 mounted on a milk collection container 5.

The breastshield 2 once again has the dimensionally stable, preferably stiff main body 25 with a milk attachment part 28 for securing on the milk collection container 5. In the main body 25, a breastshield insert 3 is once again arranged, which is preferably flexible. However, it can also be dimensionally stable, in particular stiff. Similarly, it can be designed in one piece with the breastshield 2. At its closed end 26 directed away from the breast, the insert 3 defines the receiving area 33. A lower wall of the insert 3 or of the breastshield 2 is designed as a through-opening 36. The wall is in this case preferably designed partially as a through-opening. The media separation membrane 9 is arranged below this opening. It is preferably clamped between breastshield 2 and insert element 3. The media separation membrane 9 closes the opening 36 and, depending on the applied underpressure, frees it and thus opens a milk flow path between receiving area 33 and milk collection container 5.

Located below the through-opening 36 and the media separation membrane 9 is the pump chamber 90, from which a vacuum channel 250 leads to the outside. The rest of the wall of the pump chamber 90 is formed by the main body 25 or by the milk attachment part 28. The vacuum channel 250 extends in the main body 25 or in the milk attachment part 28. Thus, the breastshield 2 also forms the media separation device.

The milk flow path or milk channel 251 leads from the through-opening 36 to the milk collection container 5. It is deflected laterally on account of the media separation membrane 9 and extends, preferably in the area near the breast, to the side of the pump chamber 90. In doing so, it preferably extends through the lowest point of the media separation membrane in the position of use, so that no milk remains lying on the membrane. This milk channel 251 can preferably be closed by a check valve 91. The check valve 91 is preferably formed in one piece with the media separation membrane 9.

Figure 9:
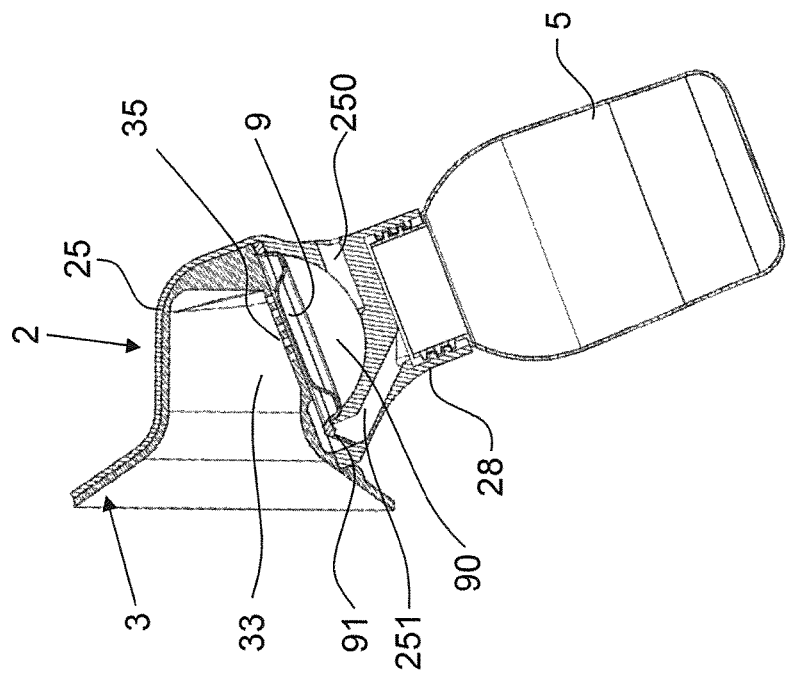
FIG. 9 shows a longitudinal section through a breastshield unit according to the invention, mounted on a milk collection container, in a third embodiment.
Figure 10:
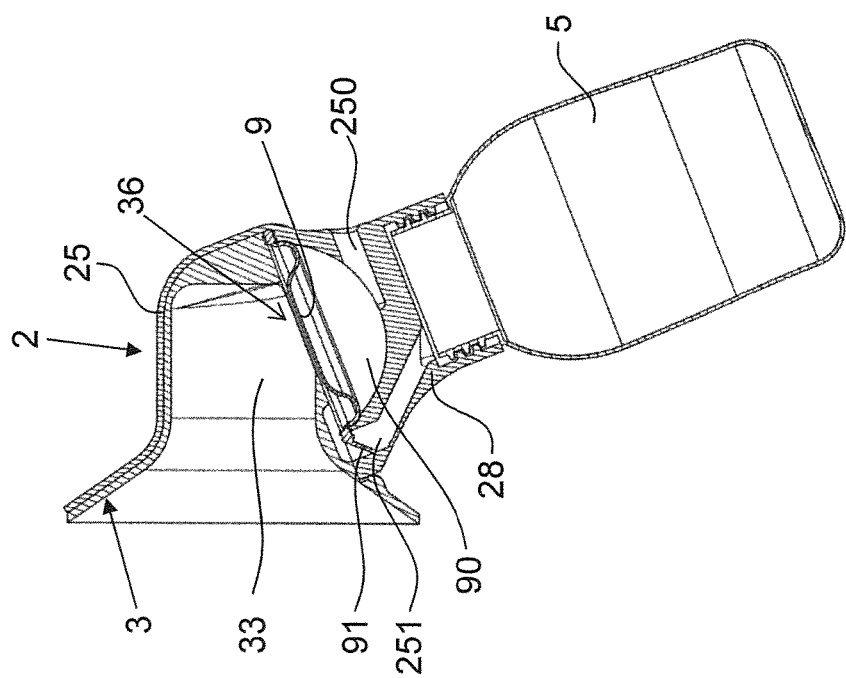
FIG. 10 shows a longitudinal section through a breastshield unit according to the invention, mounted on a milk collection container, in a fourth embodiment.

The embodiment according to FIG. 10 corresponds substantially to that according to FIG. 9. Here, however, the lower wall of the insert 3 is closed except for a few apertures 35. In this way, an upper limit for the media separation membrane 9 is provided and the nipple cannot come into contact with this membrane 9.

Despite the integrated media separation, the breastshield unit according to the invention can be made extremely compact and minimizes the dead volume.

The invention claimed is:

1. A breastshield unit for use with a breastpump for expressing human breastmilk, the breastshield unit comprising a breastshield for receiving a mother's breast and a media separation device for transferring a vacuum into an interior of the breastshield, the breastshield unit having a receiving area for receiving a nipple of the mother's breast, and the media separation device having a media separation membrane which is arranged on a rear side of the breastshield unit and which, for the purpose of transferring the vacuum, is movable to and fro between two positions, wherein the receiving area configured to receive the nipple in movement and an area of movement of the media separation device needed to transfer the vacuum partly share a same physical space, the media separation membrane being located in the receiving area at least in one of said two positions, and wherein the same physical space is configured to be occupied alternatively by the movement of the nipple and the movement of the media separation membrane, so that the nipple and the media separation membrane are not interfering with each other and wherein the media separation device as a whole is arranged to be movable relative to and inside the breastshield.

2. The breastshield unit according to claim 1, wherein a tubular stub is present which forms the receiving area and which has an end directed away from the mother's breast, wherein the media separation membrane is arranged directly on this end.

3. The breastshield unit according to claim 1, wherein the breastshield unit has an attachment for connection to a milk collection container, and wherein the media separation membrane is arranged approximately perpendicularly with respect to the attachment.

4. The breastshield unit according to claim 1, wherein a milk flow path is present which leads from the receiving area to an attachment for connection to a milk collection container, and wherein the media separation membrane is arranged in the milk flow path.

5. The breastshield unit according to claim 4, wherein the media separation membrane interrupts and re-opens the milk flow path according to a cyclically applied underpressure.

6. The breastshield unit according to claim 1, wherein the breastshield unit has an attachment for connection to a milk collection container, and wherein the media separation membrane is arranged approximately horizontally with respect to this attachment.

7. The breastshield unit according to claim 1, wherein a check valve is arranged in a milk flow path, and wherein the check valve is formed in one piece with the media separation membrane.

8. The breastshield unit according to claim 1, wherein the breastshield unit also has a breastshield insert which is securable in the breastshield, and wherein the media separation device is suspended movably by means of this breastshield insert in the breastshield.

9. The breastshield unit according to claim 1, wherein the breastshield has guide slits which extend in a longitudinal direction of the breastshield and along which the media separation device as a whole is movable.

10. The breastshield unit according to claim 1, wherein the media separation device has a dimensionally stable housing, wherein the media separation membrane is held movably therein.

11. The breastshield unit according to claim 1, wherein the breastshield has a rear opening at an end directed away from the mother's breast, as a result of which the media separation device is manually movable towards the mother's breast by access through this rear opening.

12. The breastshield unit according to claim 1, wherein the breastshield is dimensionally stable, and wherein the breastshield unit also has a flexible breastshield insert for insertion into the breastshield, wherein the breastshield has a first, open breastshield end for placing onto a mother's breast, wherein the breastshield insert has a first and a second insert end which define a longitudinal direction, wherein the first, open breastshield end has a peripheral edge on which the breastshield insert is securable to the first insert end, wherein the breastshield insert, in the assembled state, extends from this first insert end in an interior of the breastshield to the second insert end, wherein the breastshield insert, between the first and second insert ends, extends substantially spaced apart from the breastshield, and wherein the second insert end, in the assembled state of the breastshield insert, is movable in the longitudinal direction relative to the breastshield.

13. A media separation device for use in the breastshield unit according to claim 1, wherein the media separation device has a dimensionally stable housing and the media separation membrane arranged therein, and wherein the housing has a tubular receiver for receiving the breastshield or a flexible breastshield insert inserted or insertable into the breastshield, wherein this receiver defines the receiving area, the receiving area being configured to receive the nipple of a mother's breast, and wherein the media separation membrane protrudes into this receiving area, so that physical space is configured to be occupied alternatively by a movement of the nipple and a movement of the media separation membrane, so that the nipple and the media separation membrane are not interfering with each other and wherein the media separation device as a whole is arranged to be movable relative to and inside the breastshield.

14. A breastshield unit for use with a breastpump for expressing human breastmilk, the breastshield unit comprising a breastshield for receiving a mother's breast and a media separation device for transferring a vacuum into an interior of the breastshield, the breastshield unit having a breast pad for laying on the mother's breast and a receiving area for receiving a nipple of the mother's breast, and the media separation device having a media separation membrane which, for the purpose of transferring the vacuum, is movable to and fro between two positions, and which is located at a distance from the breast pad and which is a component formed separately from the breast pad, wherein the receiving area configured to receive the nipple in movement and an area of movement of the media separation device needed to transfer the vacuum partly share a same physical space, the media separation membrane being located in the receiving area at least in one of said two positions and, wherein the same physical space is configured to be occupied alternatively by the movement of the nipple and the movement of the media separation membrane, so that the nipple and the media separation membrane are not interfering with each other.

15. The breastshield unit according to claim 14, wherein the receiving area has a wall which is provided with apertures, and wherein the media separation membrane is arranged on an outer face of the wall in an area of the apertures.

* * * * *